United States Patent [19]

Callahan

[11] Patent Number: 5,776,052
[45] Date of Patent: Jul. 7, 1998

[54] LARYNGOSCOPE ADAPTED TO POSITION AND ADVANCE A FIBEROPTIC BRONCHOSCOPE

[76] Inventor: Patrick C. Callahan, 340 Parkwood Ct., Palatine, Ill. 60067

[21] Appl. No.: 770,587

[22] Filed: Dec. 19, 1996

[51] Int. Cl.$^6$ .................................................. A61B 1/267
[52] U.S. Cl. ............................................ 600/194; 600/199
[58] Field of Search .................................. 600/185, 188, 600/190, 194, 199, 200

[56] References Cited

U.S. PATENT DOCUMENTS

5,203,320  4/1993  Augustine ........................ 600/194 X
5,498,231  3/1996  Franicevic ........................ 600/194 X

OTHER PUBLICATIONS

*Fundamentals of Trachael Intubation*, James T. Roberts, M.D., Grune & Stratton, 1983, "Mechanical Aids to Intubation", Chapter 4, pp. 47–59 and Oral Intubation Techniques, Chapter 6, pp. 73–91.

*Understanding Anesthesia Equipment, Construction, Care and Complications*, Jerry A. Dorsch, M.D. and Susan E. Dorsch, M.D., Williams & Wilkins, Third Ed., 1994; "Face Masks and Airways", Chapter 13, pp. 370–373, Laryngoscopes, Chapter 14, pp. 399–437 and p. 392.

*Fiberoptic Airway Endoscopy in Anesthesia and Critical Care*, Andranik Ovassapian, M.D., Raven Press, New York, Chapter 5, "Fiberoptic Tracheal Intubation, pp. 57–79; Chapter 8, Difficult Airway", pp. 130-134 and Chapter 9, The Difficult Intubation, pp. 135–148, (1990).

"The Rigid Bronchoscope", Udaya B.S. Prakash and José P. Diaz–Jiménez, *Bronchoscopy*, Mayo Foundation, 1994, Raven Press Ltd., Chapter 4, pp. 53–69.

"Intubation What's Old, What's New", John Ross Davidson, BA, MD, FRCPC, *The Difficult Airway I*, Anesthesiology Clinics of North America, vol. 13, No. 2, Jun. 1995, pp. 377–389.

"The Bullard™ Laryngoscope", Dr. Kenneth J. Abrams, *Trauma Anesthesia Quarterly*, Anesthesiology News, Oct., 1995, pp. 44–46 and 50.

"The UpsherScope™–An Innovative New Solution to An Old Problem", Dr. Michael Upsher, *Trauma Anesthesia Quarterly*, Anesthesiology News, Oct., 1995, pp. 66–69 and 58.

"Use of the WuScope in the Trauma Patient", Dr. Izu–Lang Wu, *Trauma Anesthesia Quarterly*, Anesthesiology News, Oct., 1995, pp. 40–42 and 48.

"The Bullard Laryngoscope A New Indirect Oral Laryngoscope (Pediatric Version)", Lawrence M. Borland, MD and Margaretha Casselbrandt, MD., *Anesth. Analg.*, International Anesthesia Research Society, 1990, 70:105–8, pp. 105–108.

"Bullard Laryngoscopy for Trauma Airway Management in Suspected Cervical Spine Injuries", Kenneth J. Abrams, MD, Nalini Desia, MD, Tatyana Katsnelson, MD., *To The Editor: Anesth. Analg.*, International Anesthesia Research Society, 1992, 74:619–23, p. 623.

(List continued on next page.)

*Primary Examiner*—Jeffrey A. Smith
*Attorney, Agent, or Firm*—McAndrews, Held & Malloy, Ltd.

[57] ABSTRACT

A laryngoscope is disclosed that has a handle including a mechanism adapted to engage and advance a flexible fiberoptic tube of a bronchoscope. The mechanism is operated by the hand that grasps the handle. The laryngoscope has a blade extending from the handle which defines a surface extending from the handle to the distal end of the blade. The mechanism includes a guide which overlies the surface to define a channel through which the fiberoptic tube is advanced to the distal end of the blade. The mechanism is positioned to advance the flexible fiberoptic tube through the channel. The mechanism also displaces the guide from the surface allowing the laryngoscope to be removed from the flexible fiberoptic tube.

6 Claims, 3 Drawing Sheets

OTHER PUBLICATIONS

"A New Laryngoscope: The Combination Intubating Device", Tzu–lang Wu, M.D., Hsiu–chin Chou, M.D., *Anesthesiology*, vol. 81, No. 4, Oct. 1994, pp. 1085–1087.

"Anesthetic Management of a Patient with Obstructive Sleep Apnea Syndrome and Difficult Airway Access", Peter Biro MD, Vladimir Kaplan, MD and Konrad E. Bloch, MD; *Journal of Clinical Anesthesia*, Elsevier Science Inc., 1995, pp. 417–421.

Clinical Assessment of the Augustine Guide™ for Endotrachael Intubation, Richard J. Carr, MD and Kumar G. Belani, MBBS, MS; *Anesth Analg.*, International Anesthesia Research Society, 1994, 78, pp. 983–987.

"The Augustine Guide as a Fiberoptic Bronchoscope Guide", Philip LaTourette, MD and Vijayakshmi U. Patil, MD., *Letter to Editor: Anesth Analog*, International Anesthesia Research Society, 1993, vol. 76: pp. 1164–1165.

"The Augustine Guide™: Defining Its Usefulness", R.J. Carr, MD and K.G. Belani, *Letter to Editor: Anesth Analg*, International Anesthesia Research Society, 1995, vol. 80: pp. 848–847.

"Unanticipated Difficult Airway Secondary to Lingual Tonsillar Hyperplasia", Donald H. Jones, DO and Stephen D. Cohle, MD *Anesth Analg*, International Anesthesia Research Society, 1993, vol. 77: pp. 1285–1288.

"Awake, Blind Nasotracheal Intubation for Cesarean Section in a Patient with Autoimmune Thrombocytopenic Purpura and Iatrogenic Cushing's Syndrome", David B. Rosenberg, MD and Jeffrey B. Gross, M.D., *Anesth Analg*, International Anesthesia Research Society, 1993, vol. 77: pp. 853–855.

"An Aid in Cases of Difficult Tracheal Intubation", Claude R. Cahen, M.D., Letter to Editor: *Anesthiology*, 1991, vol. 74: p. 197.

"The Flexible Bronchoscope", Udaya B. S. Prakash and Harubumi Kato *Bronchoscopy*, Mayo Foundation, 1994, Raven Press Ltd., Chapter 5, pp. 71–80.

"Combining the Fiberoptic Bronchoscope with a Laryngoscope Blade Aids Teaching Direct Laryngoscopy", Randall W. Hentron, MD, Jeffrey Reed, MD, Jans S. Szafranski, MD, FRCA and Raghuvender Ganta, MD, FRCA, *Letter to Editor: Anesthiology*, 1995, vol. 80: p. 433.

"Fiberoptic Intubation Facilitated by a Rigid Laryngoscope", Calvin Johnson, MD, James Hunter, MD, Eric Ho, MD and Charles Bruff, CRNA, *Letter to Editor: Anesth Analg*, International Anesthesia Research Society, 1991, vol. 72: p. 714.

"Combining Fiberoptic with other Intubation Techniques—Rigid Laryngoscopy and Fiberoptic Techniques", *The Art of Fiberoptic Intubation*, Ares R. Clinics N.A. Jun. 1995, pp. 398–399.

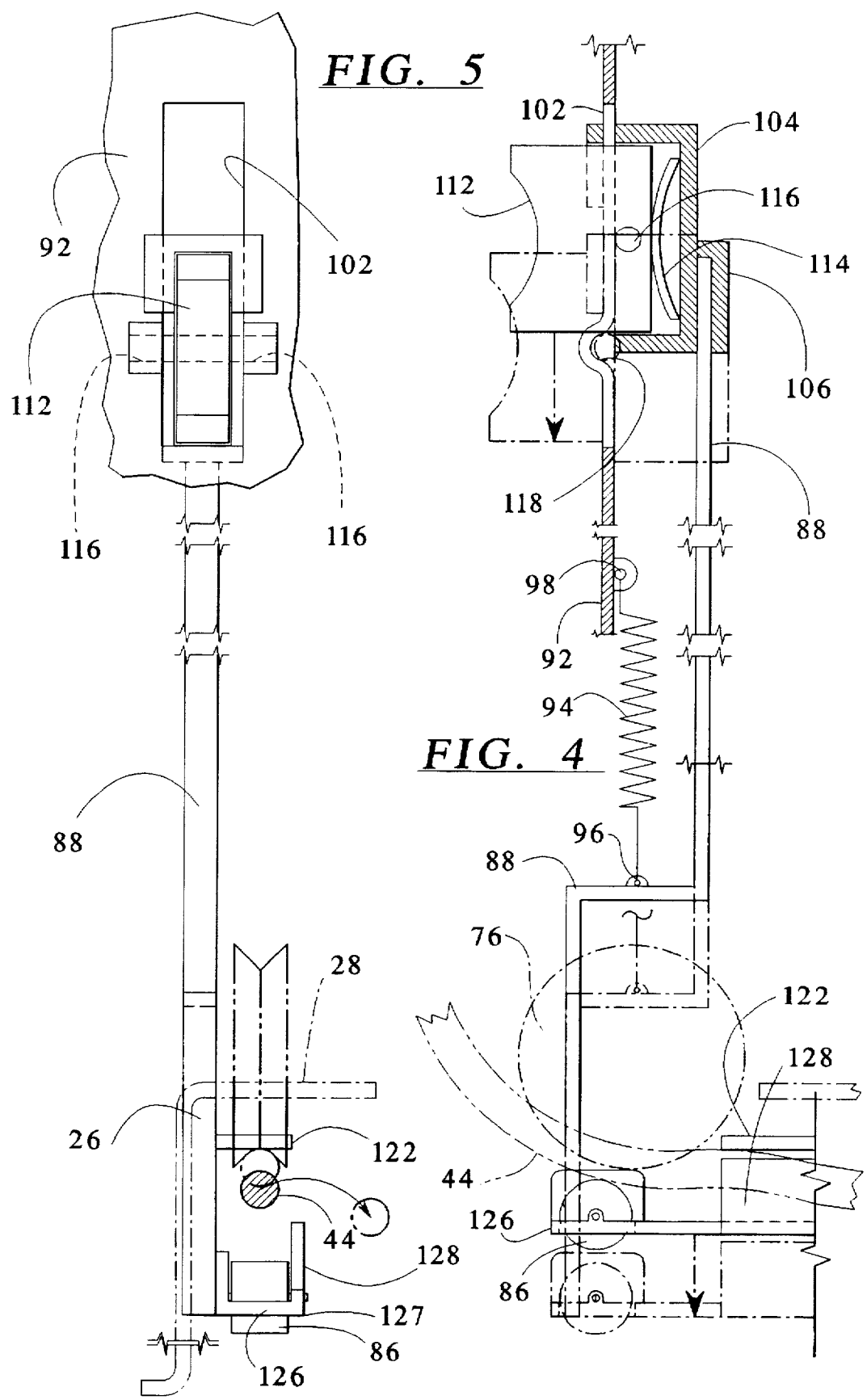

5,776,052

LARYNGOSCOPE ADAPTED TO POSITION AND ADVANCE A FIBEROPTIC BRONCHOSCOPE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The invention relates to laryngoscopes, and more particularly, to a laryngoscope adapted to receive, guide, and advance a fiberoptic bronchoscope, enabling one physician to simultaneously perform direct laryngoscopy and intubation guided by a fiberoptic bronchoscope.

Safe and effective management of a patient's airway is a critical aspect of anesthesia. Failure to maintain a patient's airway for more than a few minutes can result in brain damage or death. Airway mishaps remain the greatest source of anesthesia-related morbidity and mortality. The placement of a breathing tube in a patient's trachea (intubation) remains a crucial step in administering anesthesia.

Mechanical aids to intubation have been developed over the years. Two of the primary intubation aids are the laryngoscope and the fiberoptic bronchoscope. These devices aid the practitioner in viewing the various portions of the patient's anatomy, including the vocal cords, to assure proper placement of a breathing tube.

The earliest versions of the laryngoscope date back to the 1800s. The presently used laryngoscope consists, essentially, of a handle and a blade. The handle portion of the laryngoscope contains batteries which power a light source located in the blade. Various sizes and configurations of blades are available for use as required by a patient's anatomy.

The laryngoscope is used by the practitioner to lift the tongue, soft tissues of the oropharynx, and epiglottis to facilitate viewing of the patient's larynx when placing a breathing tube into the patients trachea. The laryngoscope is the simplest, least expensive, and by far the most frequently used aid to intubation. However, despite the laryngoscope's utility in removing proximal tissues from the field of vision, abnormalities in patient anatomy can still render intubation difficult or impossible.

Since the late 1960s, an alternative to laryngoscope aided intubation has been use of the fiberoptic bronchoscope. The fiberoptic bronchoscope uses fiberoptic technology to allow the practitioner to view the anatomy necessary to successfully place and confirm placement of a breathing tube. The fiberoptic bronchoscope conventionally has a fiberoptic tip located on the distal end of a flexible tube. Placement of the distal portion of the fiberoptic bronchoscope can be impeded by a large tongue and/or excessive soft tissue in the patient's airway. It is difficult to negotiate conventional fiberoptic bronchoscopes past these tissues.

Collapse of soft tissue making a fiberoptic intubation difficult was recognized early as a problem associated with use of fiberoptic bronchoscopes. This problem was found to be especially prevalent for the anesthetized, unconscious patient where upper airway motor tone is lost and tissue collapse is more pronounced. Several devices and maneuvers have been developed over the years to facilitate fiberoptic intubation, including using an assistant to facilitate intubation, specialized airway devices and use of a laryngoscope to manipulate tissue obstructing the fiberoptic bronchoscope.

The maneuver most commonly employed to facilitate fiberoptic intubation is physical manipulation of the patient by an assistant who attempts to lessen any tissue obstruction by providing a jaw thrust or by forcibly retracting the tongue. Such a maneuver obviously requires a trained assistant. Even when a trained assistant is available, these maneuvers may be only partially effective, depending on factors such as the patient's size, the size of the tongue and the amount of soft tissue present. The tongue pull itself is not without its own morbidity.

Fiberoptic intubation may also be facilitated by the use of various devices such as intubating airways, tongue retractors and mouth gags. An oropharyngeal airway is a disposable device which is usually made of plastic. It is inserted into the upper airway to lessen obstruction, primarily from the tongue. Several such airways are specifically designed to facilitate fiberoptic intubation (e.g., the Berman Airway, Patil-Syracuse Airway, Williams Airway Intubator and Ovassapian Fiberoptic Intubating Airway). While these devices are relatively inexpensive and easily inserted, they are also marginally effective. The greater the degree of obstruction, the less likely such intubating airways are to remove the obstruction. This is especially true when the obstruction is in the supraglottic area.

For years, various metal (malleable) L-shaped devices have been available to lift the tongue out of the way to facilitate exposure for throat examinations and procedures. Such tongue retractors have been used to perform unassisted fiberoptic intubation. The practitioner holds the head of the fiberoptic bronchoscope in one hand in the usual fashion, while the other hand holds the tip of the fiberoptic bronchoscope, as well as the tongue retractor. The tongue retractor functions to lift the tongue out of the way, while at the same time helping to place the fiberoptic bronchoscope more distally in the airway. This technique requires the practitioner to perform the difficult task of simultaneously lifting the tongue (with three fingers) while manipulating the fiberoptic bronchoscope with the thumb and index finger. This technique is cumbersome, requires additional equipment and is not as effective as a laryngoscope for soft tissue displacement.

Mouth gags, which are metal devices, are used to keep the mouth open and tongue retracted for surgical procedures of the oropharynx. Such gags have had some limited use in fiberoptic intubation but are generally not known or used by anesthesiologists. Furthermore, such devices are cumbersome and share many of the disadvantages in dealing with soft tissue displacement discussed above.

The Augustine Guide (Augstine Medical, Inc.) is a plastic device similar to a malleable tongue retractor used for blind orotracheal intubation in adults. ("Blind" means there is no direct visualization by the practitioner.) The guide, which functions to lift the tongue, contains a groove. An air-aspirating stylet is placed in the groove. The stylet is placed near and then through the vocal chords. Placement in the trachea is then verified by the positive aspiration of air. The disadvantages of the Augustine Guide include the lack of direct visualization, use of this method is restricted to adults, and an assistant is required to help retract the tongue. Some practitioners have used the groove on an Augustine Guide to place a fiberoptic bronchoscope. The fiberoptic bronchoscope must be manipulated within the Augustine Guide in the conventional manner. Furthermore, the Augustine Guide is not as effective as a laryngoscope in removing proximal tissues from the field of vision.

Practitioners have also used laryngoscopes to manipulate tissue to facilitate fiberoptic intubation. The laryngoscope provides excellent tongue and soft tissue displacement, however two practioners are generally required for intubation using both a laryngoscope and a fiberoptic bronchoscope. One practitioner holds the laryngoscope and another practitioner holds and manipulates the fiberoptic bronchoscope. While several practitioners have discussed the temporary attachment of a fiberoptic bronchoscope to a laryngoscope to view and evaluate a trainee's intubation skills, such applications involve two practitioners and do not provide any mechanism for the person holding the laryngoscope to independently advance the fiberoptic bronchoscope.

Recently, several manufacturers have combined fiberoptic technology for use with a laryngoscope. These laryngoscopes use fiberoptic technology to view the intubation process by fixing viewing lens at the distal end of the blade of the laryngoscope providing visualization from that location on the blade. There is no provision in these devices for advancing a conventional fiberoptic bronchoscope beyond the blade of the laryngoscope.

Though various aids to intubation exist, a need still exists for an instrument that can effectively manipulate tissue and provide a visualization of the patient's airway for placement and confirmation of placement of a breathing tube.

BRIEF SUMMARY OF THE INVENTION

In accordance with the present invention, disadvantages of known instruments for placement of a breathing tube in a patient's airway have been overcome. A laryngoscope is provided which accepts a flexible fiberoptic tube of a fiberoptic bronchoscope and allows a practitioner to advance the fiberoptic tube beyond the blade of the laryngoscope using only the hand that grasps the handle of the laryngoscope while simultaneously manipulating tissue with the laryngoscope in a conventional manner.

More particularly, a laryngoscope is provided that has a blade that includes a guide for a flexible fiberoptic tube along the blade to a distal location. A mechanism is mounted to the handle of the laryngoscope adjacent to a proximal opening of the fiberoptic guide of the blade. The mechanism releasably engages a flexible fiberoptic tube of a fiberoptic bronchoscope. When the mechanism engages the fiberoptic tube, the practitioner can advance and retract the fiberoptic tube along the guide of the blade by rotating a thumb wheel that is mounted to the handle of the laryngoscope and is operably connected to portion of the mechanism that engages the fiberoptic tube.

Accordingly, an object to the present invention is to provide a laryngoscope that enables a physician to accurately place a breathing tube in a patient's trachea.

Another object of the present invention is to provide a laryngoscope that is adapted to receive, advance, and retract a fiberoptic bronchoscope from the blade of the laryngoscope.

Yet another object of the invention is to provide a laryngoscope that allows a single physician to both manipulate the laryngoscope and use a fiberoptic bronchoscope to visualize a patient's airway.

A further object of the present invention is to provide a combination laryngoscope and fiberoptic bronchoscope which allows the physician to decide between standard laryngoscope intubation or fiber optic intubation instantaneously without any interruption to patient care.

Still a further object of the invention is to provide a laryngoscope with means to advance a fiberoptic bronchoscope such that a single unassisted physician can receive the benefit of the laryngoscope's maximal tongue and soft tissue control, while at the same time being able to advance a fiberoptic bronchoscope for fiberoptic intubation if desired or necessary.

These and other objects and advantages of the present invention, as well as details of the preferred embodiment thereof, will be more fully understood from the following description and the drawings.

BRIEF DESCRIPTION OF SEVERAL VIEWS OF THE DRAWINGS

FIG. 3 is a segmented back view of the laryngoscope of FIG. 1.

FIG. 4 is a side view of the mechanism of the laryngoscope of FIG. 1 showing the engaged position and the disengaged position in phantom.

FIG. 5 is a back view of the mechanism of the laryngoscope of FIG. 1.

DETAILED DESCRIPTION OF THE INVENTION

Figure 1:
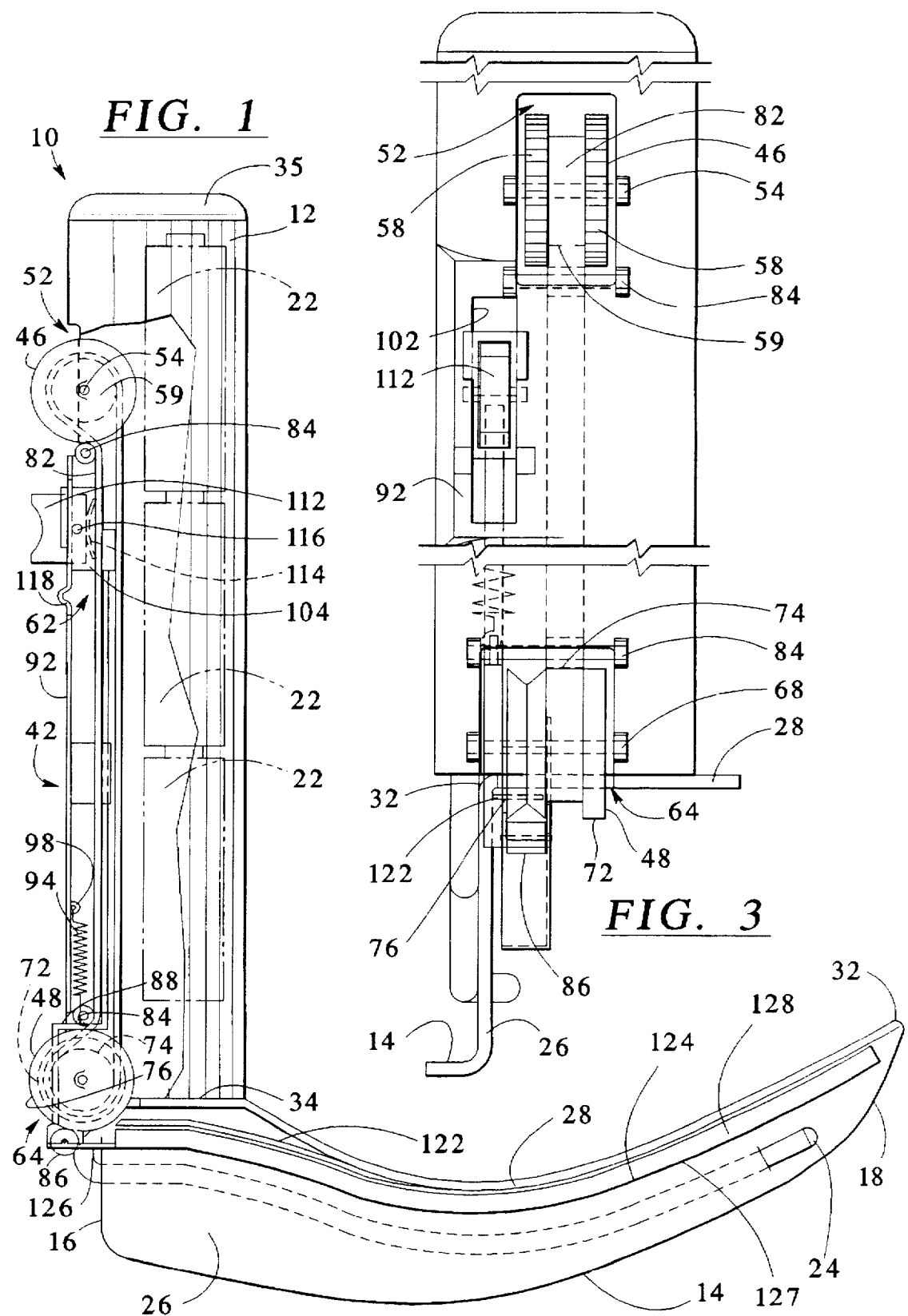
FIG. 1 is a partial cutaway side view of a laryngoscope according to the present invention having a mechanism for advancing a flexible fiberoptic tube along the blade.

FIG. 1 shows a laryngoscope 10 according to the present invention. The laryngoscope 10 includes an elongate handle 12 and a blade 14 that extends generally perpendicularly to the elongate direction of the handle 12 from a distal end 34 of the handle 12. The blade 14 is joined to the distal end 34 of the handle 12 adjacent to a proximal end 16 of the blade 14. The blade 14 extends from the proximal end 16 to a distal end 18. The blade 14 is configured to facilitate manipulation of tissue. Batteries 22 (shown in phantom by FIG. 1) are within the handle 12 and provide power to illuminate a light 24 mounted near the distal end 18 of the blade 14. Laryngoscopes configured generally as shown by FIG. 1 having batteries within the handle to power a light positioned near the distal end of the blade are well known and these aspects of the laryngoscope 10 will not be described further.

The blade 14 includes a generally flat wall 26 and a ledge 28 extending perpendicularly from the wall 26 along an edge 32 of the wall 26 that meets the end 34 of the handle 12. The ledge 28 extends from the wall 26, as is conventional for laryngoscopes, a distance sized to facilitate manipulation of tissue. That dimension is greater than a typical diameter of a flexible tube of a fiberoptic bronchoscope.

Figure 2:
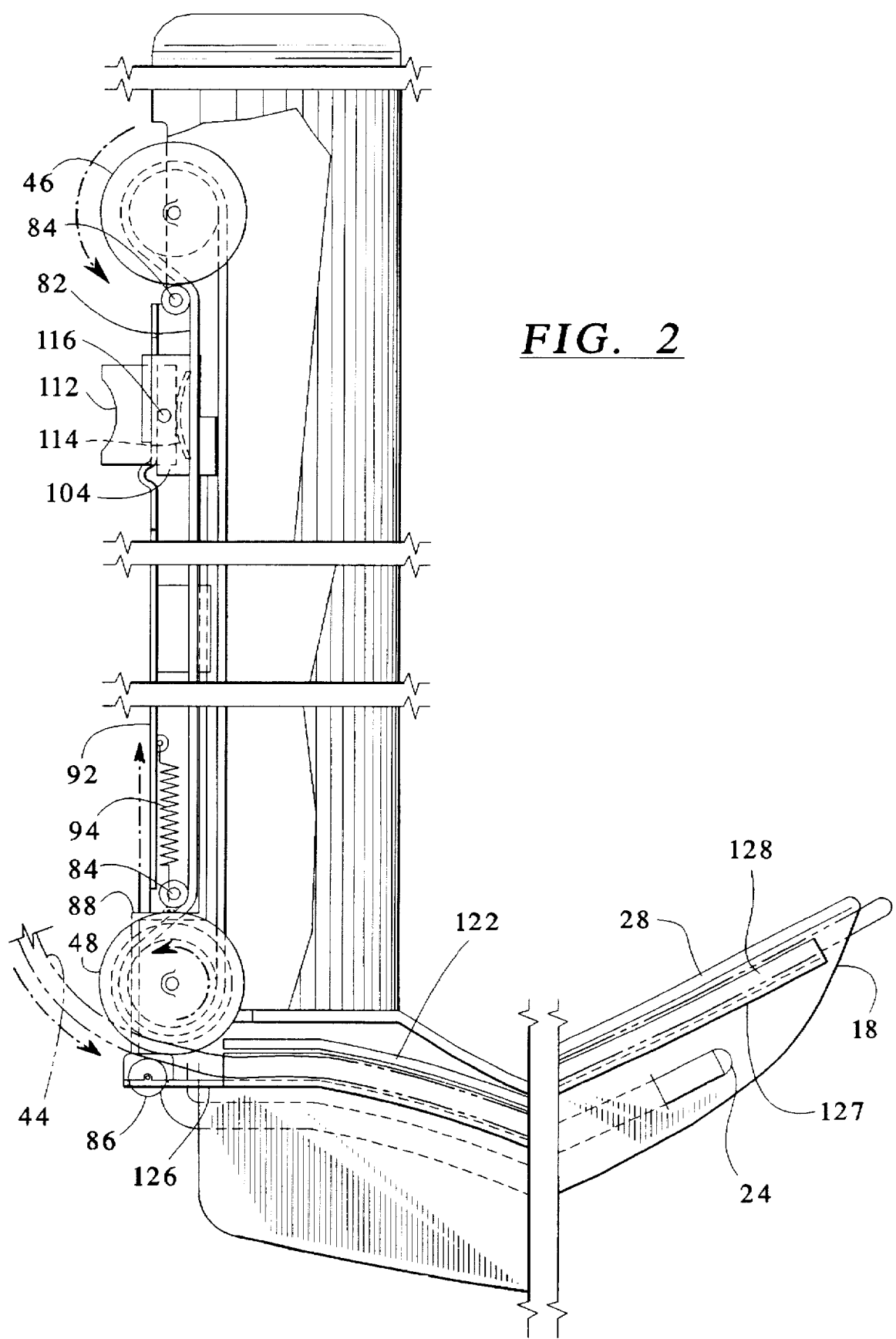
FIG. 2 is a segmented partial cutaway side view of the laryngoscope of FIG. 1 with a flexible fiberoptic tube engaged by the mechanism and extending through the blade of the laryngoscope.

The handle 12 incorporates a mechanism 42 that is adapted to capture a flexible tube 44 of a fiberoptic bronchoscope (as shown in phantom by FIG. 2). The mechanism 42 functions to capture the tube 44 adjacent to the wall 26 and advances and retracts the tube 44.

The mechanism 42 includes a thumbwheel 46 and a driven wheel 48. As best shown by FIGS. 1 and 3, the thumbwheel 46 is positioned within an opening 52 defined by the handle 12 at a location near a proximal end 35 of the handle 12 opposite the blade 14. The opening 52 opens generally opposite to the direction which the blade 14 extends from the handle 12. The thumbwheel 46 rotates about a shaft 54 which is generally perpendicular to the elongate direction of the handle 12 and to the wall 26. The shaft 54 extends through the thumbwheel 46 into opposed walls of an opening 52. As best shown by FIG. 3, the thumbwheel 46 comprises two side disks 58 of equal diameter separated by an intermediate roll 59. The radially outer edges of the side disks 58 are grooved to improve friction and allow the thumbwheel 46 to be rotated by a motion along the elongate direction of the handle 12.

As best shown by FIGS. 1 and 2, a channel 62 extends from the opening 52 along the handle 12 to a location near the distal end 34 of the handle 12. The handle 12 defines an opening 64 which opens, as does opening 52, generally opposite to the direction which the blade 14 extends from the handle 12, and opens to the end 34 of the handle 12. The channel 62 communicates with and between the openings 52 and 64.

The driven wheel 48 is positioned within the opening 64 and extends from the handle both oppositely from the blade 14, as does thumb wheel 46, and along the direction of the handle 12 beyond the end 34 of the handle 12. The driven wheel 48 rotates about a rod 68 which is parallel to the rod 54 and extends through the driven wheel 48 into opposed walls of an opening 64.

As best shown by FIG. 3, the driven wheel 48 comprises a side disk 72, a roll 74, and a drive roll 76 having a radially outer surface that defines a V groove around the circumference. The roll 74 of the driven wheel 48 and the roll 59 of the thumbwheel 46 are aligned with each other along the elongate direction of the handle 12. A flexible drive belt 82 is a continuous loop that extends through the channel 62 and wraps roll 74 of the driven wheel 48 and the roll 59 of the thumbwheel 46. The drive belt 82 extends directly between the edges of the roll 59 and the roll 74 farthest from the surface of the surface of the handle 12.

The belt 82 is guided into the channel 62 from the surfaces of the roll 59 and the roll 74 that are near the surface of the handle 12 by guide rods 84. A guide rod 84 is parallel to the rod 54 and extends into opposed walls of the opening 52 at a location adjacent to the thumbwheel 46 in the direction toward the distal end 34 of the handle 12. The belt 82 extends from the surface of the roll 59 that is outward from the handle 12 over the surface of the guide rod 84 in the opening 52 opposite the surface of the handle 12 and is thereby guided into the channel 62. Similarly, a guide rod 84 is parallel to the rod 68 and extends into opposed walls of the opening 64 at a location adjacent to the driven wheel 48 in the direction toward the proximal end 35 of the handle 12. The belt 82 extends from the surface of the roll 74 that is outward from the handle 12 over the surface of the rod 84 in the opening 64 opposite the surface of the handle 12 and into the channel 62. The belt 82 is maintained in tension so that rotation of the thumbwheel 46 is transmitted by the belt 82 to rotate of the driven wheel 48.

As best shown by FIG. 3, the drive roll 76 of the driven wheel 48 extends beyond the end 34 of the handle 12 adjacent to the wall 26 of the blade 14. As shown by FIG. 4, the flexible tube 44 (shown in phantom) of a fiberoptic bronchoscope may be positioned within the V groove of the drive roll 76 (shown in phantom).

The mechanism 42 includes a pinch roll 86 which, as best shown by FIGS. 2, 4, and 5, is positioned adjacent to the drive wheel 76 generally opposite the distal end 34 of the handle 12 and urges the flexible tube 44 toward the handle 12 to contact and engage the drive roll 76. The pinch roll 86 presses the flexible tube 44 against the drive roll 76 with a force sufficient force to engage the drive roll 76 to move with the surface of the drive roll 76. The pinch roll 86 is mounted to the end of an arm 88 to rotate about an axis that is parallel to the rod 68 about which the driven wheel 48 rotates. The arm 88 extends into the channel 62 of the handle 12.

A cover 92 overlies the channel 62 and is secured to the handle 12. As best shown by FIGS. 2 and 4, as spring 94 extends from a first end 96 that is secured to the arm 88 and extends toward the end 35 of the handle 12 to a second end 98 that is secured to the cover 92. The spring 94 urges the arm 88 toward the proximal end 35 of the handle 12 and thereby urges the pinch roll 86 toward the drive roll 76.

As best shown by FIGS. 3 and 4, the cover 92 defines an elongate opening 102 extending generally along the elongate direction of the handle. As best shown by FIG. 3, the opening 102 is adjacent to the opening 52 for the thumb wheel 46 though displaced toward the distal end 34 of the handle 12. As best shown by FIG. 4, the arm 88 extends to and is secured to a member 104 that is positioned in the channel 62 beneath the opening 102 in the cover 92. The member 104 defines a lower surface 106 that slidably abuts the channel 62. The member 104 defines an elongate opening 108 that opens adjacent to the opening 102 in the cover 92.

A button 112 is configured to conform to and is positioned within the opening 108 of the member 104. The button 112 extends from the member 104 through the opening 102 in the cover 92. A spring 114 positioned between the button 112 and the member 104 urges the button away from the member 104 and toward the cover 92. A pin 116 extends through the button 112 in a direction generally perpendicular to the elongate direction of the opening 102 in the cover 92 and extends oppositely beyond the button 112 to abut a surface of the cover 92 facing the channel 62. The pin 116 is positioned within the button 112 to allow a portion of the button 104 to extend through the opening 102 in the cover 92. The spring 114 urges the pin 116 into contact with the surface of the cover 102 adjacent to the channel 62.

As best shown by FIG. 4, the cover 102 defines two recesses 118 extending away from the channel 62. The recesses are sized to accept the pin 116 and thereby prevent the button 112, member 104, arm 88, and pinch roll 86 from translating along the elongate direction of the handle 12. The recesses 118 are positioned to receive the pin 116 when the pinch roll 86 is displaced along the elongate direction of the handle 12 away from the drive roll 76. At that location, as best shown by FIG. 4, a flexible tube 44 may be positioned adjacent to the drive roll 76 and adjacent to the ledge 28. Displacing the button 112 toward the channel 62 lowers the pin 116 into the channel 62 allowing the spring 94 to urge the arm 88, and consequently the pinch roll 86, toward the proximal end 35 of the handle 12 thereby urging the flexible tube 44 into contact with the drive roll 76.

As shown by FIG. 1, flat rail 122 extends from the wall 26 parallel to the ledge 28 from location adjacent to the drive roll 76 toward the distal end 18 of the blade 14 to join the ledge 28 at a location between the proximal end 16 and the distal end 18 of the blade 14. The rail 122 extends from the wall 26 a distance greater than the diameter of the fiberoptic flexible tube 44. The rail 122 and ledge 28, in combination, provide a continuous guide from the location adjacent to the drive wheel 76 to the distal end 18 of the blade 14.

As best shown by FIG. 1, a guide cover 124 is fixed to the arm 88 adjacent to the pinch roll 86. The guide cover 124 extends from the arm 88 along the wall 26 and is formed to extend along the rail 122 and ledge 28 to a location near the distal end 18 of the blade 14. As best shown be FIG. 5, the guide 124 includes a guide top 126 that is generally parallel to and spaced from the rail 122 and ledge 28. The guide top 126 extends along the back wall 26 and from the wall 26 to an edge 127 that is spaced from the back wall 26 a distance greater than the diameter of the flexible tube 44 of a fiberoptic bronchoscope. A guide side wall 128 extends toward the rail 122 and ledge 28 from the edge 127 of the guide top 126.

As shown by FIG. 2, the guide 122 is secured to the arm 88 to provide, in combination with the wall 26, rail 122, and ledge 28, a channel through which the flexible tube 44 of a fiberoptic bronchoscope may be advanced by the drive roll 76 to the distal end 18 of the blade 14. As shown by FIG. 4, the arm 88 is prevented from movement toward the end 35 of the handle 12 by the pinch roll 86 abutting the flexible tube 44 that is captured between the pinch roll 86 and the drive wheel 76. The side wall 128 extends to a location adjacent to the rail 122 and the ledge 28 preventing the flexible tube 44 from moving away from the wall 26. The guide top 126 prevents the flexible tube 44 from moving away from the rail 122 and ledge 28. The flexible tube 44 may be advanced to the distal end 18 of the blade 14 by the drive wheel 76 within a channel formed by the wall 26, ledge 28, rail 122, and guide 124.

As shown in phantom by FIG. 4, movement of the arm 88 toward the distal end 34 of the handle 12 displaces the pinch roll 86 from the drive roll 76 and displaces the guide 124 so that the side wall 128 displaces away from the rail 122 and ledge 128. The guide 124 displaces away from the rail 122 and the ledge 28 a distance sufficient to allow the laryngoscope 10 to be disengaged from the flexible tube 44 by moving the blade 14 away from the flexible tube 44 allowing the flexible tube 44 to pass between the guide 124 and the rail 122 and ledge 28.

In practice, the laryngoscope 10 will be used in a conventional manner to manipulate tissue. The laryngoscope may be used independently from a fiberoptic bronchoscope as a conventional laryngoscope. Preferrably, the flexible tube of a fiberoptic bronchoscope is advanced and guided to the distal end 18 of the blade 14 by the mechanism 42 and the guide 124. The fiberoptic flexible tube 44 may be advanced beyond the distal end 18 of the blade 14 and the blade 14 used to manipulate tissue in a conventional manner to facilitate placement of the fiberoptic flexible tube 44. The laryngoscope 10 may then be disengaged from the fiberoptic bronchoscope by displacing the guide 124 from the rail 122 and ledge 28. The fiberoptic flexible tube 44 may then be advanced into the trachea and a breathing tube passed along the flexible tube in a conventional manner to complete the placement of the breathing tube.

Modifications and variations of the present invention are possible in light of the above teachings. Thus, it is to be understood that, within the scope of the appended claims, the invention may be practiced other than as described above.

I claim:

1. A laryngoscope comprising:
   an elongate handle extending from a proximal end to a distal end, the handle including a mechanism having an engagement section at the distal end of the handle that is adapted to engage a flexible fiberoptic tube of a bronchoscope;
   a blade structured to manipulate the proximal tissue of a patent's airway, having a proximal end and a distal end, and secured to the distal end of the handle at a location adjacent to the proximal end of the blade;
   the blade defining a surface extending from a location adjacent to the engagement section of the mechanism along the blade to the distal end of the blade;
   the mechanism having a guide extending along the surface and structured to overlie the surface to define a channel from the engagement section to the distal end of the blade sized to accept the flexible fiberoptic tube of a bronchoscope when the a flexible fiberoptic tube is engaged by the engagement section;
   the mechanism adapted to be manually operable from the handle to advance the flexible fiberoptic tube of a bronchoscope through the channel when the fiberoptic tube is engaged by the engagement section;
   the engagement section further adapted to disengage the flexible fiberoptic tube of a bronchoscope;
   the mechanism being adapted to displace the guide from the surface a distance sufficient to allow the flexible fiberoptic tube of a bronchoscope to separate from the laryngoscope; and
   the mechanism adapted to be manually operable from the handle to cause the engagement section to disengage the flexible fiberoptic tube and to cause the guide to displace from the surface
   whereby a practitioner can grasp the handle of the laryngoscope to manipulate proximal airway tissue while viewing the region adjacent to the distal end of the blade either directly as in conventional laryngoscopy or via the flexible fiberoptic tube of a bronchoscope, can advance the flexible fiberoptic tube of a bronchoscope beyond the blade using the hand grasping the handle of the laryngoscope, and can disengage the laryngoscope from the flexible fiberoptic tube after placement of the tube within the patient's airway.

2. The laryngoscope of claim 1 wherein the engagement section comprises a drive roll rotatably mounted to the handle and a pinch roll rotatably mounted to the mechanism, the drive roll and the pinch roll rotating about parallel axes and being separated to define a space therebetween to accept the flexible fiberoptic tube, the mechanism being adapted to urge the pinch roll towards the drive roll to engage the flexible fiberoptic tube of a bronchoscope and to displace the pinch roll from the drive roll to disengage the flexible fiberoptic tube.

3. The laryngoscope of claim 2 wherein the pinch roll is mounted to an arm of the mechanism that extends from the handle and the guide is mounted to the handle whereby movement of the arm displaces the pinch roll from the guide roll and displaces the guide.

4. The laryngoscope of claim 3 wherein the pinch roll is mounted adjacent to the drive roll opposite the distal end of the handle and the mechanism includes a member mounted to the arm within the handle and a button that slidably extends from the member in a direction outward from the handle through an elongate slot in the handle whereby movement of the button toward the distal end of the handle displaces the pinch roll from the drive roll.

5. The laryngoscope of claim 4 wherein the mechanism further comprises a spring mounted between the member and the button urging the button outward from the handle and wherein the handle defines recesses structured to receive the button by an outward displacement and prevent displacement along the elongate slot at a location at which the button and member have displaced the arm and the pinch roll from the drive roll.

6. The laryngoscope of claim 2 wherein the mechanism includes a thumbwheel rotatably mounted within the handle to rotate about an axis perpendicular to the handle and extending from an outer surface of the handle to be rotated by a movement of a hand engaging the thumbwheel along the handle, the thumbwheel being operably connected to the drive wheel so that rotation of the thumbwheel rotates the drive wheel.

* * * * *